United States Patent [19]
Steffens et al.

[11] Patent Number: 6,011,145
[45] Date of Patent: Jan. 4, 2000

[54] CHAIN LENGTH SPECIFIC UDP-GLC: FATTY ACID GLUCOSYLTRANSFERASES

[75] Inventors: John C. Steffens, Chapel Hill, N.C.; Gurdev S. Ghangas, Ithaca, N.Y.; Jian-Ping Kuai, Elgin, Ill.; Nancy T. Eannetta, Newfield, N.Y.

[73] Assignee: Cornell Research Foundation, Inc., Ithaca, N.Y.

[21] Appl. No.: 09/106,464

[22] Filed: Jun. 30, 1998

Related U.S. Application Data

[60] Provisional application No. 60/055,554, Aug. 13, 1997.

[51] Int. Cl.$^7$ .................................................. C12N 15/54
[52] U.S. Cl. ..................... 536/23.2; 536/23.1; 530/370; 530/379; 435/193; 435/69.1
[58] Field of Search ................................ 536/23.2, 23.6; 530/370, 379; 435/193

[56] References Cited

U.S. PATENT DOCUMENTS 5,756,328  5/1998  Steffens et al. ........................ 435/183

FOREIGN PATENT DOCUMENTS

WO97/45546  12/1997  WIPO.

OTHER PUBLICATIONS

Chandra, G. R., et al., Biochimica et Biophysica Acta, vol. 526, pp. 387–397 (1978).

Horvath, D. M., et al., Plant Molecular Biology, vol. 31, pp. 1061–1072 (Aug. 1996).

Ghangas, G. S. and Steffens, J. C., Nat'l Acad. Sci. USA, vol. 90, pp. 9911–9915, (Nov. 1993).

Ghangas, G. S. and Steffens, J. C., Archives of Biochemistry and Biophysics, vol. 136, No. 1, pp. 370–377 (Jan. 10, 1995).

Li, X., Eannetta, N. T., Ghangas, G. S. and Steffens, J. C., Supplement to Plant Physiology, vol. 108, No. 2, p. 66, Abstract 288 (Jun. 12, 1995).

Truesdale, Mark R., et al., Plant Physiol, vol. 112, p. 446, (1996), and printout of sequence from Plant Gene Register PGR 96–064.

Kuai, J. –P., Ghangas, G. S. and Steffens, J. C., Plant Physiol., 115, 1581–1587 (1997).

*Primary Examiner*—Ponnathapu Achutamurthy
*Assistant Examiner*—Richard Hutson

[57] ABSTRACT

Enzyme activities which transfer glucose from uridine 5'-diphosphate glucose to fatty acids to form 1-O-acyl-β-glucoses which act as acyl donors in the esterification of glucose and further esterification of partially acylated glucose and in the esterification of sucrose and further esterification of partially acylated sucrose, are separated according to specificity for transferring glucose to short, medium or long chain length fatty acids. DNA molecules coding for the enzyme activities are isolated. Methods for preparing 1-O-acyl-β-D-glucoses comprise reacting uridine 5'-diphosphate glucose and fatty acid in the presence of the appropriate enzyme activity.

2 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1627 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 1..1413

(xi) SEQUENCE DESCRIPTION: SEQ ID NO:1:

```
CAA ATG GGT CAG CTA CAT TTT TTC TTC TTT CCC ATG ATG GCT CAA GGT        48
Gln Met Gly Gln Leu His Phe Phe Phe Phe Pro Met Met Ala Gln Gly
  1               5                  10                  15

CAT ATG ATA CCT ACA CTT GAC ATG GCG AAG CTT GTC GCT TGT CGT GGT        96
His Met Ile Pro Thr Leu Asp Met Ala Lys Leu Val Ala Cys Arg Gly
             20                  25                  30

GTT AAA GCC ACT ATA ATC ACA ACA CCT CTC AAT GAA TCT GTT TTC TCT       144
Val Lys Ala Thr Ile Ile Thr Thr Pro Leu Asn Glu Ser Val Phe Ser
         35                  40                  45

AAA GCT ATT GAG AGA AAC AAG CAT TTA GGT ATT GAA ATT GAT ATT CGT       192
Lys Ala Ile Glu Arg Asn Lys His Leu Gly Ile Glu Ile Asp Ile Arg
     50                  55                  60

TTA CTA AAA TTC CCA GCT AAG GAG AAT GAT TTG CCT GAA GAT TGT GAG       240
Leu Leu Lys Phe Pro Ala Lys Glu Asn Asp Leu Pro Glu Asp Cys Glu
 65                  70                  75                  80

CGT CTT GAT CTT GTA CCT TCT GAT GAC AAA CTC CCA AAC TTC TTA AAA       288
Arg Leu Asp Leu Val Pro Ser Asp Asp Lys Leu Pro Asn Phe Leu Lys
                 85                  90                  95

GCT GCG GCT ATG ATG AAA GAT GAA TTT GAG GAG CTT ATT GGA GAA TGT       336
Ala Ala Ala Met Met Lys Asp Glu Phe Glu Glu Leu Ile Gly Glu Cys
            100                 105                 110

CGC CCT GAT TGT CTT GTT TCT GAT ATG TTC CTT CCA TGG ACT ACT GAT       384
Arg Pro Asp Cys Leu Val Ser Asp Met Phe Leu Pro Trp Thr Thr Asp
        115                 120                 125

AGT GCA GCC AAA TTT AGC ATA CCA AGA ATT GTA TTC CAT GGA ACT AGT       432
Ser Ala Ala Lys Phe Ser Ile Pro Arg Ile Val Phe His Gly Thr Ser
    130                 135                 140

TAC TTT GCG CTT TGT GTT GGC GAT AGC ATC AGG CGT AAT AAG CCT TTC       480
Tyr Phe Ala Leu Cys Val Gly Asp Ser Ile Arg Arg Asn Lys Pro Phe
145                 150                 155                 160

AAG AAT GTG TCA TCG GAT ACT GAA ACT TTT GTT GTA CCG GAT TTT CCA       528
Lys Asn Val Ser Ser Asp Thr Glu Thr Phe Val Val Pro Asp Phe Pro
                165                 170                 175

CAT GAA ATT AGG CTA ACT AGA ACA CAG TTG TCT CCG TTT GAG CAA TCG       576
His Glu Ile Arg Leu Thr Arg Thr Gln Leu Ser Pro Phe Glu Gln Ser
            180                 185                 190

GAT GAA GAG ACG GGT ATG GCT CCC ATG ATT AAA GCT GTG AGG GAA TCG       624
Asp Glu Glu Thr Gly Met Ala Pro Met Ile Lys Ala Val Arg Glu Ser
        195                 200                 205

GAT GCG AAG AGC TAT GGA GTT ATA TTC AAT AGC TTT TAT GAG CTT GAA       672
Asp Ala Lys Ser Tyr Gly Val Ile Phe Asn Ser Phe Tyr Glu Leu Glu
    210                 215                 220
```

```
TCA GAT TAT GTT GAA CAT TAC ACT AAG GTT GTA GGT AGA AAA AAT TGG      720
Ser Asp Tyr Val Glu His Tyr Thr Lys Val Val Gly Arg Lys Asn Trp
225                 230                 235                 240

GCT ATT GGT CCG CTT TCG CTG TGC AAT AGG GAT ATT GAA TAT AAA GCG      768
Ala Ile Gly Pro Leu Ser Leu Cys Asn Arg Asp Ile Glu Tyr Lys Ala
                245                 250                 255

GAA AGA GGG AGG AAA TCA TCT ATC GAT GAA CAC GCG TGC TTG AAA TGG      816
Glu Arg Gly Arg Lys Ser Ser Ile Asp Glu His Ala Cys Leu Lys Trp
            260                 265                 270

CTT GAT TCG AAG AAA TCA AGT TCC ATT GTT TAT GTT TGT TTT GGA AGT      864
Leu Asp Ser Lys Lys Ser Ser Ser Ile Val Tyr Val Cys Phe Gly Ser
        275                 280                 285

ACA GCA GAT TTC ACT ACA GCA CAG ATG CAA GAA CTT GCT ATG GGG CTA      912
Thr Ala Asp Phe Thr Thr Ala Gln Met Gln Glu Leu Ala Met Gly Leu
    290                 295                 300

GAA GCC TCT GGA CAA GAT TTC ATT TGG GTT ATC AGA ACA GGG AAT GAA      960
Glu Ala Ser Gly Gln Asp Phe Ile Trp Val Ile Arg Thr Gly Asn Glu
305                 310                 315                 320

GAT TGG CTC CCA GAA GGA TTC GAG GAA AGA ACA AAA GAA AAA GGT TTA     1008
Asp Trp Leu Pro Glu Gly Phe Glu Glu Arg Thr Lys Glu Lys Gly Leu
                325                 330                 335

ATC ATA AGA GGA TGG GCA CCC CAA GTG CTG ATT CTT GAT CAC GAA GCT     1056
Ile Ile Arg Gly Trp Ala Pro Gln Val Leu Ile Leu Asp His Glu Ala
            340                 345                 350

ATT GGA GCT TTT GTT ACT CAT TGT GGA TGG AAC TCG ACA CTG GAA GGA     1104
Ile Gly Ala Phe Val Thr His Cys Gly Trp Asn Ser Thr Leu Glu Gly
        355                 360                 365

ATA TCA GCA GGG GTA CCA ATG TTG ACA TGG CCA GTA TTT GCG GAA CAG     1152
Ile Ser Ala Gly Val Pro Met Leu Thr Trp Pro Val Phe Ala Glu Gln
    370                 375                 380

TTT TTC AAT GAG AAG TTG GTG ACT GAG GTA ATG AGA AGT GGA GCT GGT     1200
Phe Phe Asn Glu Lys Leu Val Thr Glu Val Met Arg Ser Gly Ala Gly
385                 390                 395                 400

GTT GGT TCT AAG CAA TGG AAG AGA ACA GCT AGT GAA GGA GTG AAA AGA     1248
Val Gly Ser Lys Gln Trp Lys Arg Thr Ala Ser Glu Gly Val Lys Arg
                405                 410                 415

GAA GCA ATA GCA AAG GCG ATA AAG AGA GTA ATG GCG AGT GAA GAA ACA     1296
Glu Ala Ile Ala Lys Ala Ile Lys Arg Val Met Ala Ser Glu Glu Thr
            420                 425                 430

GAG GGA TTC AGA AGC AGA GCA AAA GAG TAC AAA GAA ATG GCA AGA GAA     1344
Glu Gly Phe Arg Ser Arg Ala Lys Glu Tyr Lys Glu Met Ala Arg Glu
        435                 440                 445

GCT ATT GAA GAA GGA GGA TCA TCT TAC AAT GGA TGG GCT ACT TTG ATA     1392
Ala Ile Glu Glu Gly Gly Ser Ser Tyr Asn Gly Trp Ala Thr Leu Ile
    450                 455                 460

CAA GAC ATA ACT TCA TAT CGT TAACTAGTGA TGCAAAAAAA AGAAAAAACA        1443
Gln Asp Ile Thr Ser Tyr Arg
465                 470

TGTGTGTTTC TATATTCTGT CTTCTGTTTT GCTGATTTGA TCATATTACG TACTTCTTCA   1503

TCATAATTAA TGCATCAAT AGAATCCAAG ATCAATCATC TCGAAATTCA ACGTTAAAAT    1563

ATTCGACATT TGAATAATAC ATCGAATTAA AATGGAAAAA AAAAAAAAAA AAAAAAAAAA   1623

AAAA                                                                1627

(2) INFORMATION FOR SEQ ID NO:2:

(i) SEQUENCE CHARACTERISTICS:
        (A) LENGTH: 471 amino acids
        (B) TYPE: amino acid
        (D) TOPOLOGY: linear
```

(ii) MOLECULE TYPE: protein (xi) SEQUENCE DESCRIPTION: SEQ ID NO:2:

```
Gln Met Gly Gln Leu His Phe Phe Phe Pro Met Met Ala Gln Gly
 1               5                  10                  15

His Met Ile Pro Thr Leu Asp Met Ala Lys Leu Val Ala Cys Arg Gly
            20                  25                  30

Val Lys Ala Thr Ile Ile Thr Thr Pro Leu Asn Glu Ser Val Phe Ser
                35                  40                  45

Lys Ala Ile Glu Arg Asn Lys His Leu Gly Ile Glu Ile Asp Ile Arg
         50                  55                  60

Leu Leu Lys Phe Pro Ala Lys Glu Asn Asp Leu Pro Glu Asp Cys Glu
 65                  70                  75                  80

Arg Leu Asp Leu Val Pro Ser Asp Asp Lys Leu Pro Asn Phe Leu Lys
                 85                  90                  95

Ala Ala Ala Met Met Lys Asp Glu Phe Glu Glu Leu Ile Gly Glu Cys
            100                 105                 110

Arg Pro Asp Cys Leu Val Ser Asp Met Phe Leu Pro Trp Thr Thr Asp
            115                 120                 125

Ser Ala Ala Lys Phe Ser Ile Pro Arg Ile Val Phe His Gly Thr Ser
130                 135                 140

Tyr Phe Ala Leu Cys Val Gly Asp Ser Ile Arg Arg Asn Lys Pro Phe
145                 150                 155                 160

Lys Asn Val Ser Ser Asp Thr Glu Thr Phe Val Val Pro Asp Phe Pro
                165                 170                 175

His Glu Ile Arg Leu Thr Arg Thr Gln Leu Ser Pro Phe Glu Gln Ser
            180                 185                 190

Asp Glu Glu Thr Gly Met Ala Pro Met Ile Lys Ala Val Arg Glu Ser
            195                 200                 205

Asp Ala Lys Ser Tyr Gly Val Ile Phe Asn Ser Phe Tyr Glu Leu Glu
        210                 215                 220

Ser Asp Tyr Val Glu His Tyr Thr Lys Val Val Gly Arg Lys Asn Trp
225                 230                 235                 240

Ala Ile Gly Pro Leu Ser Leu Cys Asn Arg Asp Ile Glu Tyr Lys Ala
                245                 250                 255

Glu Arg Gly Arg Lys Ser Ser Ile Asp Glu His Ala Cys Leu Lys Trp
            260                 265                 270

Leu Asp Ser Lys Lys Ser Ser Ile Val Tyr Val Cys Phe Gly Ser
        275                 280                 285

Thr Ala Asp Phe Thr Thr Ala Gln Met Gln Glu Leu Ala Met Gly Leu
290                 295                 300

Glu Ala Ser Gly Gln Asp Phe Ile Trp Val Ile Arg Thr Gly Asn Glu
305                 310                 315                 320

Asp Trp Leu Pro Glu Gly Phe Glu Glu Arg Thr Lys Glu Lys Gly Leu
                325                 330                 335

Ile Ile Arg Gly Trp Ala Pro Gln Val Leu Ile Leu Asp His Glu Ala
            340                 345                 350

Ile Gly Ala Phe Val Thr His Cys Gly Trp Asn Ser Thr Leu Glu Gly
        355                 360                 365

Ile Ser Ala Gly Val Pro Met Leu Thr Trp Pro Val Phe Ala Glu Gln
    370                 375                 380

Phe Phe Asn Glu Lys Leu Val Thr Glu Val Met Arg Ser Gly Ala Gly
385                 390                 395                 400

Val Gly Ser Lys Gln Trp Lys Arg Thr Ala Ser Glu Gly Val Lys Arg
```

-continued

```
                    405                     410                         415

Glu Ala Ile Ala Lys Ala Ile Lys Arg Val Met Ala Ser Glu Glu Thr
            420                 425                 430

Glu Gly Phe Arg Ser Arg Ala Lys Glu Tyr Lys Glu Met Ala Arg Glu
            435                 440                 445

Ala Ile Glu Glu Gly Gly Ser Ser Tyr Asn Gly Trp Ala Thr Leu Ile
    450                 455                 460

Gln Asp Ile Thr Ser Tyr Arg
465                 470
```

CHAIN LENGTH SPECIFIC UDP-GLC: FATTY ACID GLUCOSYLTRANSFERASES

CROSS-REFERENCE TO RELATED APPLICATION

This application claims the benefit of U.S. Provisional Application No. 60/055,554, filed Aug. 13, 1997.

The invention was made at least in part with United States Government support under United States Department of Agriculture Grant Number NRICGRP 94-37300-0390. The United States Government has certain rights in the invention.

TECHNICAL FIELD

The invention is directed to purified uridine 5'-diphosphate (i.e., UDP)-glucose: fatty acid glucosyltransferase activities which are chain length specific, to isolated DNA molecules producing these activities, and to methods of preparing 1-O-acyl-β-glucoses.

BACKGROUND OF THE INVENTION

Ghangas, G. S. and Steffens, J. C., Proc. Natl. Acad. Sci. USA, Vol. 90, pp 991–9915 (November 1993) describes results which it states suggest that polyacylated glucoses are obtained in wild tomato (*Lycopersicon pennelli*) in a multistep mechanism where the first step involves activation of fatty acids via UDP-glucose-dependent reaction to form 1-O-acyl-β-glucose and succeeding steps involve transfer of the 1-O-acyl moiety of 1-O-acyl-β-glucose to non-anomeric positions of other glucose or partially acylated glucose molecules. Ghangas and Steffens found that *L. pennellii* leaf extracts catalyzed formation of 1-O-isobutyryl-β-D-glucose, 1-O-lauroyl-β-D-glucose and 1-O-palmitoyl-β-D-glucose.

SUMMARY OF THE INVENTION

The invention herein is directed to or involves purified enzyme activities which activate free fatty acids by catalyzing formation of high energy state 1-O-acyl-β-glucose. In particular, the enzyme activities transfer glucose from uridine 5'-diphosphate (UDP) glucose to fatty acids to form the 1-O-acyl-β-glucose. The 1-O-acyl-β-glucoses act as acyl donors in the esterification of glucose and in the further esterification of partially acylated glucose in reactions catalyzed by glucose acyltransferases. The 1-O-β-glucoses act as acyl donors in the esterification of sucrose and in the further esterification of partially acylated sucrose in reactions catalyzed by sucrose acyltransferases.

The above-described activities are denoted herein as UDP-glucose:fatty acid glucosyltransferase activities. The enzyme activities of the invention are more specific for reaction with certain chain length fatty acids than with other fatty acids. Multiple enzyme activities having different specificities, have been discovered.

In one embodiment herein, denoted the first embodiment herein, the purified UDP-glucose:fatty acid glucosyltransferase activity is more specific to $C_3$–$C_5$ fatty acids including straight chain and branched chain fatty acids and saturated and unsaturated fatty acids, than to longer chain fatty acids, and has a $V_{max}/K_m$ at least eight times as great for reaction of uridine 5'-diphosphate glucose (UDPG) with isobutyrate as with laurate or palmitate and has a specific activity of at least 200 units/mg, preferably at least 1,000 units/mg.

In another embodiment herein, denoted the second embodiment herein, the purified UDP-glucose:fatty acid glucosyltransferase activity is more specific to $C_6$–$C_{13}$ fatty acids including straight chain and branched chain fatty acids and saturated and unsaturated fatty acids, than to shorter chain fatty acids and longer chain fatty acids, and has a $V_{max}/K_m$ at least eight times as great for reaction of uridine 5'-diphosphate glucose with laurate as with isobutyrate or palmitate and has a specific activity of at least 200 units/mg, preferably at least 350 units/mg.

In another embodiment herein, denoted the third embodiment herein, the purified UDP-glucose:fatty acid glucosyltransferase is more specific to $C_{14}$–$C_{22}$ fatty acids including straight chain and branched chain fatty acids and saturated and unsaturated fatty acids, than to shorter chain fatty acids, and has a $V_{max}/K_m$ at least eight times as great for reaction of uridine 5'-diphosphate glucose with palmitate as with isobutyrate or laurate and has a specific activity of at least 200 units/mg.

In the description of the embodiments above, $V_{max}$ and $K_m$ are determined from Lineweaver-Burk reciprocal plots, and the $K_m$ for fatty acids are determined at 5 mM uridine 5'-diphosphate glucose, and the $K_m$ for uridine 5'-diphosphate glucose is determined at 5 mM isobutyrate, 610 μM laurate and 200 μM palmitate.

For kinetic studies and determination of specific activities, assaying is carried out as follows: The standard assay mixture contains 2.5 μM Bis-Tris, pH 6.8, 75 nmol uridine 5'-diphosphate glucose, 0.067% (v/v) Triton X-100, 5×10⁵ dpm $^{14}$C-fatty acid (about 55 mCi/mmol) and 5 μl of enzyme in a total volume of 15 μl in 0.65-ml polypropylene tubes. $^{14}$C-Fatty acid is dried in the tube, 10 μl of reaction mixture (no enzyme) is added, tubes are vortexed briefly, sonicated in a water bath until turbidity disappears, then enzyme is added. Mixtures are incubated at 37 degrees C for two hours. Five μl of each reaction mixture are analyzed by silica gel TLC (samples are developed with chloroform/methanol/$H_2O$, 75:22:3, and autoradiographed overnight or longer, and the areas corresponding to radioactive bands are eluted with ethanol/$H_2O$, 1:1, for liquid scintillation counting). For kinetic studies, the incubation is carried out at 37° C. for 45 minutes and the reaction is terminated by boiling.

One unit of enzyme activity is defined herein as the amount of enzyme producing one nmol of 1-O-acyl-β-glucose in one hour in the above described assay.

In another embodiment herein, denoted the fourth embodiment herein, UDP-glucose:fatty acid glucosyltransferase activities are purified and separated from extracts from source plants by steps comprising polyethylene glycol protein precipitation (to precipitate protein that is not of interest) and subjecting resulting supernatant to ion exchange chromatography, e.g., on a DEAE-Sepharose column to separate activities according to fatty acid chain length specificity. The separated activities are each preferably further purified by affinity chromatography.

In another embodiment herein, denoted the fifth embodiment herein, there is provided a DNA molecule encoding UDP-glucose:fatty acid glucosyltransferase of the first embodiment herein.

In another embodiment herein denoted the sixth embodiment herein, there is provided a DNA molecule encoding UDP-glucose:fatty acid glucosyltransferase of the second embodiment herein.

In another embodiment herein denoted the seventh embodiment herein, there is provided a DNA molecule encoding UDP-glucose:fatty acid glucosyltransferase of the third embodiment herein.

In another embodiment herein, denoted the eighth embodiment herein, there is provided a method of preparing 1-O-acyl-β-D-glucose where the acyl contains 3 to 5 carbon atoms and is straight or branched chain, saturated or unsaturated, comprising reacting uridine-5'-diphosphate glucose and $C_3$–$C_5$ straight or branched chain saturated or unsaturated fatty acid or salt or ester thereof in the presence of a catalytically effective amount of UDP-glucose:fatty acid glucosyltransferase of the first embodiment herein.

In another embodiment herein, denoted the ninth embodiment herein there is provided a method of preparing 1-O-acyl-β-D-glucose where the acyl contains 6 to 13 carbon atoms and is straight or branched chain, saturated or unsaturated, comprising reacting uridine-5'-diphosphate glucose and $C_6$–$C_{13}$ straight or branched chain saturated or unsaturated fatty acid or salt or ester thereof in the presence of a catalytically effective amount of UDP-glucose:fatty acid glucosyltransferase of the second embodiment herein.

In another embodiment herein, denoted the tenth embodiment herein, there is provided a method of preparing 1-O-acyl-β-D-glucose where the acyl contains 14 to 22 carbon atoms and is straight or branched chain, saturated or unsaturated, comprising reacting uridine-5'-diphosphate glucose and $C_{14}$–$C_{22}$ straight or branched chain saturated or unsaturated fatty acid or salt or ester thereof in the presence of a catalytically effective amount of the UDP-glucose:fatty acid glucosyltransferase of the third embodiment herein.

DETAILED DESCRIPTION

The sources for the purified enzyme activities include the leaves of *L. pennellii* (wild tomato), *L. esculentum* (cultivated tomato), corn, wheat, rape, bean, melon, and cucumber.

A preferred source for enzyme activities of the first, second and third embodiments is *L. pennellii* (LA 1376). Seeds for this variety were originally deposited with and obtainable from Tomato Genetics Resource Center, Department of Vegetable Crops, University of California Davis 95616-8746 and are readily grown in a greenhouse. The "LA" designation is the Lycopersicon accession number. Thus, *L. pennellii* (LA 1376) can be designated *L. pennellii* (Lycopersicon Accession No. 1376). The original seed was collected on Dec. 30, 1970 by Dr. Charles Rick at Sayan (Department Lima), Peru and was deposited and accessioned in 1971. The sample size was seven plants out of a population of twenty plants and the plants were found growing at 1,000 meters elevation along a dry rocky slope. *L. pennellii* (LA 1376) is preferred because it grows very vigorously.

Another source for enzyme activities of the first, second and third embodiments is *L. pennellii* (LA 716). Seeds for this variety were originally deposited with and are obtainable from Tomato Genetics Resource Center, Department of Vegetable Crops, University of California Davis 95616-8746 and are readily grown in a greenhouse. The "LA" designation is the Lycopersicon accession number. Thus, *L. pennellii* (LA 716) can be designated *L. pennellii* (Lycopersicon Accession No. 716). The original seed was collected on Feb. 16, 1958 by Donovan Correll at the Pacific face of the southern Peruvian Andes (latitude, 16 degrees south, by longitude 73–74 degrees west) and deposited and accessioned in 1959. The plant of LA 716 is described at pages 39–41 of Correll, Donovan Stewart, "The Potato and Its Wild Relative," Texas Research Foundation, Renner, Tex. 1962.

Another source of enzyme activities of the first, second and third embodiments is *L. esculentum* cv. VFNT Cherry. Seeds are available from Tomato Genetics Resource Center, Department of Vegetable Crops, University of California Davis.

Another source of enzyme activities of the first, second, and third embodiments is an F1 population of *L. pennellii* (LA716) and *L. esculentum* (cv New Yorker) cross. Seeds for *L. esculentum* (cv New Yorker) are available from USDA Plant Genetic Resources Unit, New York State Agricultural Experiment Station, Geneva, N.Y. 14456.

A source of enzyme activities of the third embodiment is the rape plant, genus *Brassica napus* L. See Mandava N., et al., Chem. Ind. 930–931 (1972). Seeds are available from USDA Plant Genetic Resources Unit, New York State Agricultural Experiment Station, Geneva, N.Y. 14456.

UDP-glucose:fatty acid glucosyltransferase activities have been purified from *L. pennellii* leaf extracts and have been separated in a first case representing the first embodiment herein into activity which shows higher specificity toward short chain fatty acids as represented by isobutyrate than toward medium chain fatty acids as represented by octanoate and laurate and in a second case representing the second embodiment herein into activity which shows higher specificity toward medium chain fatty acids as represented by octanoate and laurate than toward short chain fatty acids as represented by isobutyrate.

The activity of the first case catalyzes the reaction of uridine 5'-diphosphate glucose (UDP-glucose) and short chain fatty acid (i.e., $c_3$–$C_5$ fatty acid) to form 1-O-short chain acyl-D-glucose more efficiently than the reaction of uridine 5'-diphosphate glucose and medium chain fatty acid to form 1-O-medium chain acyl-D-glucose. The reaction may be carried out in a reaction mixture of 50 mM Tris-HCl (pH 7.0), 10 mM mgCl$_2$, 10 mM dithiothreitol, 10 mM UDP-glucose and 1 mM fatty acid.

The activity of the second case catalyzes the reaction of uridine 5'-diphosphate glucose (UDP-glucose) and medium chain fatty acid to form 1-O-medium chain acyl-D-glucose more efficiently than the reaction of uridine 5'-diphosphate glucose and short chain fatty acid to form 1-0-short chain acyl-D-glucose. The reaction may be carried out in a reaction mixture of 50 mM Tris-HCl (pH 7.0), 10 mM mgCl$_2$, 10 mM dithiothreitol, 10 mM UDP-glucose and 1 mM fatty acid.

In the first case, a purified UDP-glucose:fatty acid glucosyltransferase activity is provided, having a $V_{max}/K_m$ at least eight times as great for reaction of uridine 5'-diphosphate glucose with isobutyrate as with octanoate and with laurate.

In the second case, a purified UDP-glucose:fatty acid glucosyltransferase activity is provided, having a $V_{max}/K_m$ at least eight times as great for reaction of uridine 5'-diphosphate glucose with octanoate and with laurate as with isobutyrate.

Both kinds of activities have also been found in leaf extracts from cultivated tomato *L. esculentum*.

The activity of the first case has been purified more than 3,000-fold from *L. pennellii* leaf extract. Such activity purified from *L. pennellii* leaf extract has $M_r$ of 47,000 as determined by chromatography on Sephacryl S-200 native gel and about the same $M_r$ when analyzed by SDS-PAGE, indicating monomeric enzymatic structure. Such activity does not bind strongly to either UDP-agarose or UDP-glucuronic acid agarose. When a sample obtained following DEAE-Sepharose chromatography is submitted to chromatofocusing or isoelectric focusing, much of the activity is lost. It has a pI as determined by chromatofocusing to be about 5.0. When it is chromatographed on a Mono-Q HPLC column, no activity is recovered. It does not bind to octyl-Sepharose. It does not bind to Concanavalin A-Sepharose. Such activity purified from L. pennellii leaf extract has a $V_{max}/K_m$ of 10.4 for isobutyrate, a $V_{max}/K_m$ of 1.01 for octanoate and a $V_{max}/K_m$ of 0.82 for laurate.

The activity of the second case has been purified 300-fold from L. pennellii leaf extract. Such activity purified from L. pennellii leaf extract has an $M_r$ of 47,000 as determined by chromatography on Sephacryl S-200 native gel and about the same $M_r$ when analyzed by SDS-PAGE, indicating monomeric enzymatic structure. It does not bind to Concanavalin A-Sepharose. Such activity purified from L. pennellii leaf extract has a $V_{max}/K_m$ of 0.27 for isobutyrate, a $V_{max}/K_m$ of 6.77 for octanoate and a $V_{max}/K_m$ of 2.60 for laurate.

Partial purification and separation of the two kinds of activities (i.e., of the first and second embodiments herein) are obtained from L. pennellii by subjecting leaf extracts thereof to a three-step purification process. In the first step, leaf extract is admixed with polyethylene glycol (molecular weight 3,350) to precipitate protein that is not of interest. In the second step, supernatant containing the remaining protein is subjected to ion exchange chromatography, e.g., on a DEAE-Sepharose column to recover two pools of fractions: one pool of fractions with activity of the first kind, i.e., with higher specificity toward short chain fatty acids; and a second pool of fractions with activity of the second kind, i.e., with higher specificity toward medium chain fatty acids. In the third step, each separated activity is subjected to affinity chromatography, e.g., on Cibacron blue 3GA agarose columns, to further purify both of the activities.

Enzyme activity representing the third embodiment herein, that is which is more specific to $C_{14}$-$C_{22}$ fatty acids than to shorter chain fatty acids, can be separated and purified from leaves of L pennellii LA1376 by polyethylene glycol precipitation of leaf extract to remove proteins that are not of interest, and by separation of the remaining portion on a DEAE-Sepharose column, assaying each fraction for uridine 5 -diphosphate-glucose-dependent transglycosylation activity toward radiolabeled $C_{14}$–$C_{22}$ fatty acids of choice. Finally, the separated activity is subjected to affinity chromatography, e.g., on a Cibacron blue 3GA agarose column to further purity the activity. The activity of the third embodiment catalyzes the reaction of uridine 5'-diphosphate glucose (UDP-glucose) and long chain fatty acids (i.e., $C_{14}$–$C_{22}$ fatty acids) to form 1-O-long chain acyl-D-glucose more efficiently than the reaction of uridine 5'-diphosphate glucose and shorter chain fatty acids to form 1-O-shorter chain acyl-D-glucose. The reaction may be carried out in a reaction mixture of 50 mM Tris-HCl (pH 7.0), 10 mM mgCl$_2$, 10 mM dithiothreitol, 10 mM UDP-glucose and 1 mM fatty acid.

In the eight, ninth and tenth embodiments herein the reactions may be carried out in the presence of Tris-HCl (pH 7.0) as a buffer, MgCl$_2$ (as a protein stabilizer) and dithiothreitol (as a protein stabilizer and antioxidant). The uridine 5'-diphosphate glucose is preferably present in excess to drive the reaction to completeness, e.g., in a 10:1 or a 15:1 molar ratio with the fatty acid. The glucosyltransferase may be present, for example, in an amount of 1 to 20 units of enzyme per 15 μl of reaction volume.

We turn now to isolation of DNA molecules coding for UDP-glucose:fatty acid glucosyltransferase of the first, second, and third embodiments herein. This is carried out by a method comprising the steps of preparing a cDNA library from leaf trichome or leaf mRNA, and immunoscreening using antibody to the enzymatic activity being sought.

A detailed description of the isolation and identification of cDNA encoding for UDP-glucose:fatty acid glucosyltransferase is set forth in Example III hereinafter.

cDNA of the ninth embodiment herein, in the case of cDNA isolated in Example III, has a sequence comprising the sequence set forth in the Sequence Listing as SEQ ID NO:1.

UDP-glucose:fatty acid glucosyltransferase of the second embodiment herein in the case of protein corresponding to cDNA isolated in Example III, has a sequence comprising the sequence set forth in the Sequence Listing as SEQ ID NO:2.

Uridine 5'-diphosphate glucose is commercially available.

The invention is illustrated by the following examples.

EXAMPLE I

All procedures were carried out at 4° C. L. pennellii (Lycopersicon accession number LA1376; seeds originally deposited with and obtainable from Tomato Genetics Resource Center, Department of Vegetable Crops, University of California Davis 95616-8746) leaves (0.5 kg) were homogenized with 750 ml of extraction buffer (A) containing 75 mM HEPES, pH 7.5, 0.25 M sucrose, 10 mM dithiothreitol (DTT), 1 mg/ml diethyldithiocarbamic acid, sodium salt (DIECA) and 1% (w/v) acid washed polyvinylpolypyrrolidone (PVPP), the homogenate filtered through four layers of cheesecloth, and the filtrate centrifuged at 15,000 g for 20 min. Polyethylene glycol (PEG) 3,350 was added to the supernatant at 0.22 g/ml. After the PEG was completely dissolved, the protein extract was centrifuged at 15,000 g for 15 min and pellet was discarded. PEG was then added to a final concentration of 0.37 g/ml and the resulting solution was centrifuged again at 15,000 g for 15 min to pellet the protein. The pellet was resuspended in about 80 ml of buffer (B) containing 50 mM HEPES, pH 7.5, 20% glycerol (v/v), 0.2 mM phenylmethanesulfonylfluoride (PMSF) and 10 mM DTT, and the suspension was clarified by centrifugation at 30,000 g for 5 min. The pellet was washed once with buffer (B) to recover residual protein and the two supernatants were combined and loaded onto a DEAE-Sepharose column (1×20 cm) pre-equilibrated with buffer (B). After extensive washing with buffer (B) (about 150 ml), bound protein was eluted with a 100 ml linear gradient of 0 to 0.3 M NaCl in buffer (B). Two-ml fractions were collected and assayed for UDPG:fatty acid glucosyltransferase activity using [$^{14}$C]-isobutyrate and [$^{14}$C]-laurate as described above. Fractions were organized into two pools: those exhibiting enhanced activity towards either [$^{14}$C]-isobutyrate or [$^{14}$C]-laurate (GTI and GTII, respectively). These pooled activities were desalted separately on Econo-Pac 10DG desalting columns (Bio-Rad), diluted two-fold and then loaded to Cibacron blue 3GA agarose columns (1×3 cm) pre-equilibrated with buffer (C) (50 mM HEPES, pH 7.5, 20% glycerol [v/v], 5 mM DTT and 0.2 mM PMSF), respectively. The two columns were washed with five bed volumes of buffer (B). The glucosyltransferase activities were then eluted with 2 mM UDPG in buffer (C). The active fractions were pooled, concentrated by dialyzing against solid PEG 20,000, and dialyzed extensively against buffer (C). Glycerol was added to the samples up to 30% (v/v) and the enzymes were then stored at −20° C.

GTI activity determined in the initial extract and total protein, total GTI activity, and specific GTI activity determined initially and after each purification stage and degree of GTI purification and GTI yield determined after each purification stage, with assays for enzyme activity being carried out as described above, for 1-O-isobutyryl-β-glucose, are set forth in Table 1 below:

TABLE 1

| Step | Total Protein mg | Total Activity units | Specific Activity units/mg | Fold Purification | % Yield |
|---|---|---|---|---|---|
| Crude extract | 3075 | 1071 | 0.348 | | |
| PEG (0.22–0.37 g/ml) pellet | 183 | 815 | 4.45 | 12.8 | 76.0 |
| DEAE-sepharose | 31.5 | 564 | 17.9 | 5.4 | 52.7 |
| Cibacron Blue 3GA-agarose | 0.222 | 261 | 1175 | 3376 | 24.4 |

GTII activity determined in the initial extract and total protein, total GTII activity, and specific GTII activity determined initially and after each purification stage and degree of GTII purification and GTII yield after each purification stage, with assays for enzyme activity being carried out as described above, for 1-O-lauroyl-β-glucose, are set forth in Table 2 below:

TABLE 2

| Step | Total Protein mg | Total Activity units | Specific Activity units/mg | Fold Purification | % Yield |
|---|---|---|---|---|---|
| Crude extract | 3075 | 4536 | 1.48 | | |
| PEG (0.22–0.37 g/ml) pellet | 183 | 1452 | 7.93 | 5.36 | 32.00 |
| DEAE-sepharose | 41.4 | 1034 | 25.0 | 16.9 | 22.8 |
| Cibacron Blue 3GA-agarose | 0.211 | 94 | 445 | 300 | 2.1 |

GTI did not bind strongly to either UDP-agarose or UDP-glucuronic acid agarose. When a GTI sample obtained following DEAE-Sepharose chromatography was submitted to chromatofocusing (Polybuffer Exchanger, Pharmacia, pH 4–6) or isoelectric focusing (Bio-Rad Rotofor, pH 4–6), much of the activity was lost; however, the pI of GTI was determined by chromatofocusing to be about 5.0. When a partially purified GTI preparation (PEG precipitation, followed by DEAE-Sepharose and Cibacron Blue 3GA agarose chromatography) was chromatographed on a Mono-Q (Pharmacia) HPLC column, no activity was recovered. GTI did not bind to octyl-Sepharose. Neither GTI nor GTII bound to Concanavalin A-Sepharose. Both GTI and GTII possessed $M_r$ of 47,000 when chromatographed on Sephacryl S-200, and exhibited similar $M_r$ when analyzed by SDS-PAGE, indicating the monomeric structure of these enzymes. Activity was doubled in the presence of 10 mM $Mn^{2+}$, and increased ca. 50% by the same concentration of $Mg^{2+}$.

Kinetic parameters determined for GTI and GTII are set forth in Table 3 below where "UDP-Glc" stands uridine 5,'-diphosphate glucose.

TABLE 3

| Substrate | $K_m$ μM | $V_{max}$ units/mg | $V_{max}/K_m$ (×10$^{-3}$) |
|---|---|---|---|
| GTI | | | |
| UDP-Glc | 108[b] | | |
| isobutyrate (i4:0) | 230 | 2.389 | 10.4 |
| octanoate (8:0) | 538 | 0.543 | 1.01 |
| laurate (12:0) | 660 | 0.540 | 0.82 |
| GTII | | | |
| UDP-Glc | 126[c] | | |
| isobutyrate (i4:0) | 789 | 0.215 | 0.27 |
| octanoate (8:0) | 87.9 | 0.595 | 6.77 |
| laurate (12:0) | 196 | 0.509 | 2.60 |

[a]All $K_m$ determinations for fatty acids used 5 mM UDP-Glc.
[b]Determined at 5 mM isobutyrate.
[c]Determined at 610 μM laurate.

GTII showed higher activity towards long-chain fatty acids (16:0, 18:1, 18:2) than did GTI, although $K_m$ and $V_{max}$ data (not shown) indicated these acids were substantially poorer substrates for GTII than 8:0 and 12:0.

EXAMPLE II

All procedures are carried out at 4° C. *L. pennelli* (Lycopersicon accession number 1376; seeds originally deposited with and obtainable from Tomato Genetics Resource Center, Department of Vegetable Crops, University of California Davis 95616-8746) leaves (0.5 kg) are homogenized with 750 ml of extraction buffer (A) containing 75 mM HEPES, pH 7.5, 0.25 M sucrose, 10 mM dithiothreitol (DTT), 1 mg/ml diethyldithiocarbamic acid, sodium salt (DIECA) and 1% (w/v) acid washed polyvinylpyrrolidone (PVPP). The homogenate is filtered through four layers of cheesecloth, and the filtrate is centrifuged at 15,000 g for 20 minutes. PEG is added to the supernatant at 0.22 g/ml. After the PEG is completely dissolved, the protein extract is centrifuged at 15,000 g for 15 minutes and the resulting pellet is discarded. PEG is then added to a final concentration of 0.35 g/ml, and the resulting solutions centrifuged at 15,000 g for 15 minutes to pellet the protein. The pellet is suspended in about 80 ml buffer (B) containing 50 mM HEPES, pH7.5, 20% glycerol (v/v), 0.2 mM polymethanesulfonylfluoride (PMSF) and 10 mM DTT, and the suspension is clarified by centrifugation at 30,000 g for 5 minutes. The pellet is washed once with buffer (B) to recover residual protein and the two supernatants are combined and loaded onto a DEAE-Sepharose column (1×20 cm) pre-equilibrated with buffer (B). After extensive washing with buffer (B) (about 150 ml) bound protein is eluted with 200 ml linear gradient of 0 to 0.3 M NaCl in buffer (B). Two-ml fractions are collected and assayed for UDPG fatty acid glucosyltransferase activity as described above using [$^{14}$C]-palmitic acid. The pooled palmitate-specific glucosyltransferase activities are desalted on a Econo-Pac 10 DG desalting column (Bio Rad), diluted two-fold and then loaded to Cibacron blue 3GA Agarose columns (1×3 cm) pre-equilibrated with buffer (C) (50 mM HEPES, pH7.5, 20% glycerol (v/v), 5 mM DTT and 0.2 mM PMSF). The column is then washed with three bed volumes of buffer (B), and eluted with a linear gradient of 0 to 10 mM UDPG in buffer (C) (5 ml). The active fractions are pooled, concentrated by dialyzing against solid PEG 20,000 and dialyzed extensively against buffer (C). Glycerol is added to the samples to 30% (v/v) and the enzyme is stored at –20° C. The isolated enzyme activity shows higher activity towards long-chain fatty acids (16:0, 18.1, 18.2) than GTI and GTII and has a $V_{max}/K_m$ at least at times as great for reaction of uridine 5'-diphosphate glucose with palmitate as with isobutyrate or laurate and has a specific activity of at least 200 units/mg.

EXAMPLE III

A cDNA expression library was prepared from leaf trichome mRNA of an F1 population of *L. pennellii* (LA 716) and *L. esculentum* (cv New Yorker) cross, using a lambda-ZAP-cDNA Synthesis Kit (Stratagene, 11011 North Torrey Pines Rd., La Jolla, Calif.). The leaf trichome mRNA was obtained as follows: Detached trichomes were obtained from the leaves by dry ice abrasion as described in Yerger, E. H., et al., Plant Physiol. 99, 1–7 (1992) except that pulverized dry ice was first seived through a fiberglass screen (1.4 mm$^2$ mesh). The trichomes were suspended in freshly prepared Tris-HCl, pH 7.0 (buffer)/1 mM MgCl$_2$ (stabilizer of protein structure and enzymatic activity)/0.1% diethyldithiocarbamate (acts as copper chelator to inhibit polyphenol oxidase)/ 0.1% dithiothreitol (acts as copper chelator to inhibit polyphenol oxidase and as scavenger of quinones, the reaction product of polyphenol oxidase)/2% polyvinylpyrrolidone (inhibitor of polyphenl oxidase; acts as scavenger of phenolics, the substrates for polyphenol oxidase). Total RNA was extracted from the trichomic suspension and mRNA was purified according to the method described in Hunt, M. D., et al., Plant Molec. Biol. 21, 59–68 (1993).

Immunoscreening of the trichome cDNA library cloned in lambda-ZAP was carried out as described in the picoBlue Immunoscreening Kit instruction manual from Stratagene. The host bacteria for the phage was XL1-Blue *E. coli* MRF' strain from Stratagene. Phage were plated at a concentration of approximately 20,000 pfu/plate, and a total of about 600,000 were present for screening. After an initial incubation at 42° C., plates containing phage were placed at 37° C. and overlaid with nitrocellulose membranes that had been soaked in 10 mM isopropyl-1-thio-β-D-galactopyranoside (IPTG), an inducer of the promoter which causes expression of protein), and air dried. Plates remained at 37° C. for an additional 3.5 hours, at which point the nitrocellulose was removed and washed three times, for 15 minutes each, with TBST (25 mM Tris-HCl, pH 7.5; 5 mM MgCl$_2$ 137 mM NaCl; 0.05% (v/v) Tween 20). Nitrocellulose membranes were treated with 3% (w/v) sodium m-periodate for 10 minutes and washed once more with TBST. After washing, membranes were blocked for at least one hour with 1.0% bovine serum albumin (BSA) in TBS (TBST minus the Tween) to prevent non-specific adsorption of primary antibody to the membrane, then placed in primary antibody to GTII activity (isolated in Example I) at a 1/500 (v/v) dilution. The primary antibody had been treated with *E. coli* phage lysate, as described in the protocol, prior to use. After one hour in primary antibody, membranes were washed four times for 5 minutes each in TBST, followed by a one hour incubation in a secondary antibody, namely goat-antirabbit IgG linked to alkaline phosphatase (1/1000 in blocking solution to prevent non-specific adsorption of the secondary antibody to the nitrocellulose membrane), and four more washes in TBST with one final wash in TBS. All washings and antibody incubation were at room temperature with gentle agitation. Plates containing phage were stored at 4° C. Nitrocellulose membranes were blotted to remove excess moisture and placed one at a time in freshly made developer solution (0.1 M NaHCO$_3$, pH9.8; 1.0 mM MgCl$_2$; 0.3 mg/ml nitroblue tetrazolium; 0.15 mg/ml 5-bromo-4-chloro-3-indolyl phosphate) until positives were clearly visible (about 5 minutes). Positive plaques were removed from the plate using a sterile pipet tip and placed in 0.5 ml of SM buffer (0.1 M NaCl; 8 mM Mg SO$_4$; 50 mM Tris-HCl, pH 7.5; 0.1% (w/v) gelatin) and 20 µl chloroform, vortexed and stored at 4° C. The positives were used as a basis for selecting the sites in the original plate from which the plaques were derived and phage from these sites was used to reinfect *E. coli* and the cycle was repeated twice more.

At the end of the third cycle, selection was obtained of the appropriate cDNA which was harbored in bacteriophage which in turn was harbored in *E. coli*. Then plasmid PGTII consisting of *E. coli* with cDNA insert encoding GTII, was obtained by excising the plasmid from the bacteriophage using Stratagene's Rapid Excision Kit. Clones were sequenced using automated dideoxy terminator DNA sequencing giving the sequence set forth in the Sequence Listing as SEQ ID NO:1. The sequence of the protein coded for by the cDNA of SEQ ID NO:1 is given in SEQ ID NO:2. The plasmid PGTII was sent to the American Type Culture Collection, 12301 Parklawn Drive, Rockville, Md. 20852 for deposit under the terms of the Budapest Treaty on Jun. 7, 1998 and the deposit was received by the American Type Culture Collection on Jun. 9, 1998 and was assigned accession number 209895.

Plasmid with insert encoding GTI activity is obtained the same as described above but using primary antibody to GTI instead of primary antibody to GTII.

Plasmid with insert encoding UDP-glucose:fatty acid glucosyltransferase of the third embodiment herein is obtained the same as described above except for using antibody to UDP-glucose:fatty acid glucosyltransferase of the third embodiment as the primary antibody.

EXAMPLE IV

A reaction mixture of 50 mM Tris-HCl (pH 7.0), 10 mM MgCl$_2$, 10 mM dithiotheritol 10 mM uridine 5'-diphosphate glucose, 1 mM isobutyrate, 2 units of GTI activity is made up. Reaction is carried out for 2 hrs. at 37° C. 1-O-isobutyryl-β-D-glucose is formed.

When an equimolar amount of lauric acid is substituted for the isobutyrate and 2 units of GTII is used in place of the GTI, 1-O-lauroyl-β-D-glucose is formed.

When an equimolar amount of palmitic acid is substituted for the isobutyrate and 2 units of the glucosyltransferase of the third embodiment herein is used in place of GTI, 1-O-palmitoyl-β-D-glucose is formed.

The text of related Provisional Application No. 60/055,554 filed Aug. 13, 1997, including the appendix thereto, is incorporated herein by reference.

Many variations of the above will be obvious to those skilled in the art. Thus, the invention is defined by the claims.

What is claimed is:

1. An isolated DNA molecule encoding a protein having uridine 5'-diphosphate-glucose:fatty acid glucosyltransferase activity which has a $V_{max}/K_m$ at least eight times as great for reaction of uridine 5'-diphosphate glucose with laurate as with isobutyrate or palmitate, wherein said protein comprises the amino acid Sequence of SEQ. ID NO:2.

2. An isolated DNA molecule as claimed in claim 1 which comprises the sequence set forth in the Sequence Listing as SEQ ID NO:1.

* * * * *